United States Patent [19]

Kanojia

[11] 4,060,604
[45] Nov. 29, 1977

[54] ISOLATION OF UTERO-EVACUANT SUBSTANCES FROM PLANT EXTRACTS

[75] Inventor: Ramesh M. Kanojia, Somerville, N.J.

[73] Assignee: Ortho Pharmaceutical Corporation, Raritan, N.J.

[21] Appl. No.: 726,860

[22] Filed: Sept. 27, 1976

[51] Int. Cl.² .................... A61K 35/78; A61K 31/335
[52] U.S. Cl. .................................... 424/195; 260/333; 424/278
[58] Field of Search ................. 424/195, 278; 260/333

[56] References Cited

U.S. PATENT DOCUMENTS 3,639,589  2/1972  Groebel .................................. 424/95

*Primary Examiner*—Sam Rosen
*Attorney, Agent, or Firm*—Benjamin F. Lambert

[57] ABSTRACT

A method of obtaining utero-evacuant substances from the zoapatle plant is described. The method involves the isolation and purification of biologically active compounds from the zoapatle plant by selective derivatization of purified material obtained from the plant.

16 Claims, No Drawings

ISOLATION OF UTERO-EVACUANT SUBSTANCES FROM PLANT EXTRACTS

In co-pending application Ser. No. 672,918 filed Apr. 2, 1976, which is a continuation-in-part of application Ser. No. 547,415 filed Feb. 6, 1975 and now abandoned, there is described a method of isolating and purifying extracts of the zoapatle plant which leads to purified material having useful biological activity. The method involves chromatography of the crude material through a column of adsorbent material followed by chromatography through a column of an organic polymeric gel. The present invention relates to a method of isolating and purifying the purified biologically active materials obtained from the above process by selective chemical derivatization of the semi-purified material obtained from the plant.

The zoapatle plant is a bush about 2 m. high that grows wild in Mexico. Botanically it is known as *Montanoa tomentosa* according to Cervantes, Fam. Compositae, Tribe Heliantheae; another variety of the species is *Montanoa floribunda*. The plant is described in great detail in *Las Plantas Medicinales de Mexico*, third edition, Ediciones Botas (1944).

The plant has been used for centuries in the form of a "tea" or other crude aqueous preparations primarily as a labor inducer or menses inducer for humans. Its use has been documented in the literature, but definitive chemical and pharmacological studies have not been performed.

In the current folk use of the zoapatle plant, the user typically drinks a bitter tasting "tea" brewed from the leaves of the plant by boiling them with water in the same manner used to prepare a hot beverage. She normally does this after having missed a menstrual period and thus is presumably pregnant, although it is known that many frankly pregnant women use the tea to terminate an unwanted pregnancy. The "tea" obviously contains a mixture of complex materials many of which may be undesirable and unnecessary to produce the desired effect. Natural plant substances are generally known to be exceedingly complex in their composition. Many compounds of similar chemical and physical properties, as well as those with strikingly dissimilar properties, are normally found in these substances and generally present a difficult separation and identification task.

In the above-mentioned co-pending application, a method is described for purification of crude extracts from the zoapatle plant which results in a purified material having biological activity and containing at least three components. This semi-purified material is the starting material for the present invention.

By means of the present invention, two chemically distinct compounds having utero-evacuant properties are obtained by selective chemical derivatization of the semi-purified material described above. by utero-evacuant is meant an agent which causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated.

The semi-purified material obtained in Ser. No. 547,415 contains at least three components, one of which has an $\alpha,\beta$-unsaturated keto system and the other a $\beta,\gamma$-unsaturated keto system as determined from I.R. and N.M.R. analyses of the mixture. According to the present invention, treatment of the semi-purified material with a peracid under controlled conditions epoxidizes the $\beta,\gamma$-unsaturated keto system but leaves the $\alpha,\beta$-unsaturated keto system unchanged. The epoxide which forms is separated from the $\alpha,\beta$-unsaturated ketone by techniques known to those skilled in the art. Chromatography is the preferred method. The $\beta,\gamma$-unsaturated ketone is subsequently regenerated by deoxygenation of the epoxide.

In accordance with the present invention, the epoxidation with a peracid is carried out under controlled conditions which allow selective derivatization of one of the components present in the semi-purified material. A slight excess of the peracid is employed for the epoxidation step. Generally about 1.2 equivalents are employed per equivalent of the compound containing the $\beta,\gamma$-unsaturated keto system. The reaction is perferably carried out in an organic solvent at a temperature between 0° C and room temperature from a period of about 15 mins. to about 2 hours. It is preferred to carry out the reaction at a temperature between 0°–10°, however. Any of the commercially available or commonly prepared peracids may be employed. Suitable peracids include peracetic acid, perphthalic acid, perbenzoic acid, trifluoroperacetic acid and the like. Suitable organic solvents which may be employed include halohydrocarbons such as, for example, chloroform and methylene chloride, lower alkyl ethers such as, for example, diethyl ether, diisopropyl ether, cyclic ethers such as tetrahydrofuran and dioxane, lower alkyl esters such as ethyl acetate, propyl acetate, ethyl propionate and the like and hydrocarbons such as benzene, petroleum ether, cyclohexane and the like.

The utero-evacuant materials present in the semipurified starting material each contain two hydroxyl groups as determined by I.R. an N.M.R. analyses. Although the epoxidation reaction can be carried out on a mixture of the free alcohols, if desired, the hydroxyl groups can be blocked by a protecting group prior to the epoxidation step. Protecting the allylic hydroxyl group by converting it to an acetate, for example, further reduces the susceptibility of that allylic double bond to epoxidation. Suitable protecting groups which may be employed include an acyl group such as acetyl or propionyl, a tetrahydropyranyl group, a trityl group, a silyl group or a t-butyl group. Where a protecting group is employed, the protecting group can be removed by techniques known to those skilled in the art. For example, the acyl group can be removed by treating the ester with a solution of an aqueous base such as an ammonium or alkali metal hydroxide or carbonate, the tetrahydropyranyl, trityl and silyl groups can be removed by reaction with aqueous acid solutions such as acetic acid, propionic acid, butyric acid and the like or a dicarboxylic acid such as oxalic acid or succinic acid, for example. The silyl group can also be removed under neutral condition by treating the compound with a fluoride anion in tetrahydrofuran or dimethylformamide and the t-butyl group by reaction with trifluoroacetic acid.

The epoxide is separated from other materials in the reaction mixture by techniques known to those skilled in the art. The preferred method is by chromatography, either by preparative thin layer chromatography or column chromatography. Adsorbents which may be employed for the chromatography include neutral or acidic silica gel, neutral or acidic alumina, fluorosil, organic polymer gels such as vinyl acetate copolymer, cross-linked dextran and polystyrene gels, for example. A variety of solvents may be employed for the chromatography step. Suitable solvents include polar solvents such as ethanol, propanol, butanol, ethyl acetate, butyl acetate, acetone, methyl ethyl ketone and the like and non-polar solvents such as chloroform, methylene chloride, carbon tetrachloride, pentane, hexane, cyclohexane, heptane, benzene, toluene and the like. Combinations of the above solvents may also be employed. The particular solvent or combination of solvents employed will depend upon the type of adsorbent used to separate the epoxidized material. It is preferred to employ silica gel as the adsorbent and an increasing gradient of ethyl acetate in cyclohexane as the solvent. Where column chromatography is employed for the separation, it is preferred to monitor the composition of the fractions obtained by thin layer chromatography on silver nitrate impregnated silica gel GF plates. However, the fractions can also be monitored by gas chromatography or any other suitable means for detecting the presence of the reaction products. As a result of the chromatographic procedure, two chemically distinct compounds are obtained as evidenced by gas chromatography and spectral analysis. One of the compounds contains the epoxide ring while the other contains the α,β-unsaturated system.

Regeneration of the β,γ-unsaturated keto system from the epoxide is effected by treating the epoxide with zinc-copper couple in a lower alkyl alcohol such as methanol, ethanol or propanol at reflux temperature or with triphenylphosphine selenide and trifluoroacetic acid in a chlorohydrocarbon solvent such as chloroform, for example, at room temperature. Regeneration of the β,γ-unsaturated keto system can also be accomplished by treating the epoxide at room temperature with an aqueous methanolic solution of potassium selenocyanate or octacarbonyldicobalt. Lithium diphenylphosphide may also be employed for the deoxygenation step. In addition, deoxygenation can be accomplished with a solution of iron compounds prepared by adding n-butyl lithium to a solution of iron chloride in tetrahydrofuran at −78° or with hexamethyldisilane and potassium methoxide in hexamethylphosphoric triamide at a temperature of about 50°-75° c.

The utero-evacuant properties of the isolated materials are determined by measuring the extent of uterine contractions and the degree to which pregnancy is interrupted in female animals.

The purified utero-evacuant compounds are effective when administered in doses ranging from 1.0 mg. to about 100 mg./kg. The actual dosage employed will depend upon the species of animal to which the compound is administered. The compounds can be administered in formulations prepared according to acceptable pharmaceutical practices. Suitable formulations would include solutions, suspensions and solid dosage forms.

The following describes the invention in greater particularity and is intended to be a way of illustrating but not limiting the invention.

PREPARATION OF STATING MATERIAL

Zoapatle leaves (10 kg.) and water (30 gallons) are added to a 100 gallon steam-jacketed stainless steel tank. The mixture is heated at 98°-100° C for 2.5 hours with periodic stirring. The hot mixture is filtered through gauze to afford a clear dark tea (about 25 gallons). The solid residue in the tank is washed with hot water (4 gallons), filtered, and the filtrate combined with the tea obtained above. The combined aqueous extracts are extracted with ethyl acetate (30 gallons). The mixture is stirred vigorously and allowed to settle. The top frothy layer is siphoned off to break the emulsion, and as much ethyl acetate separated as possible. Additional ethyl acetate (20 gallons) is added to the mixture and the above process is repeated. The combined ethyl acetate extracts are evaporated at 50° C under vacuum. The residue is extracted with three portions of hot (75°-80°) benzene (10 liters total). The benzene extracts are evaporated at 50° C under vacuum and the residue is washed three times with refluxing hexane (a total of 8 liters). The hexane washed residue is dissolved in acetone (2 liters), Nuchar (10 g.) is added, and the mixture is stirred 1 hour at room temperature. The charcoal is removed by filtration, and the filtrate evaporated by distillation at 30° C under vacuum to afford the crude extract (69 g.).

The crude extract (50 g.) is dissolved in ether (5 l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in. × 4 ft.) of 2.5 kg. of neutral silicic acid packed in chloroform. The column is eluted with chloroform, chloroform-isopropanol mixtures, and fractions are collected. The fractions are evaporated to dryness in vacuo at a temperature below 40° C. The column is eluted as follows:

| Fraction | Volume/Fraction (ml.) | Eluent | |
|----------|-----------------------|--------|---|
| 1-7 | 650 | CHCl$_3$ | |
| 8-30 | 500 | isopropanol:CHCl$_3$ | (1:41.7) |
| 31-60 | 500 | isopropanol:CHCl$_3$ | (1:33.3) |
| 61-105 | 500 | isopropanol:CHCl$_3$ | (1:28.6) |

The composition of the fractions is monitored by thin layer chromatography [silica gel, isopropanol-chloroform (1:12.5)] and by gas chromatography — 3% OV17 [methyl silicone:phenyl silicone (1:1)] column using a programmed run (150°-250°). Fractions Nos. 78-84 are combined and the solvent removed in vacuo to afford an oily residue of the semi-purified material (5.1 g.) which contains at least three components as indicated by gas chromatography.

EXAMPLE 1

Preparation of Epoxide

Acetic anhydride (6 ml.) is added to a solution of the semi-purified material (1 g.) in dry pyridine (12 ml.). The reaction mixture is allowed to stand under nitrogen at room temperature for 15-20 hours. The reaction mixture is then evaporated to dryness and the residue thus obtained is chromatographed on silica gel using an increasing gradient of ethyl acetate in cyclohexane as a solvent to isolate the acetylated compounds (0.8 g.). The fractions containing the acetates are combined and the solvent is removed in vacuo. The residue is dissolved in methylene chloride (12 ml.) and the solution is cooled to 0°-5° C. To this solution is added a solution of m-chloroperbenzoic acid (0.31 g.) in methylene chloride (15 ml.). The mixture is stirred at 0°-5° C for 2 hours, washed with dilute aqueous sodium bicarbonate solution, dried over sodium sulfate and evaporated to dryness. A portion of this residue is subjected to preparative thin layer chromatography on silica gel (Quantagram PQ1F) using ethyl acetate:cyclohexane (30:70) as the eluent to develop the plates. The principal uv absorbing bane (Rf~0.7–0.8) is the $\alpha,\beta$-enone diacetate and the principal non-uv-absorbing band (Rf~0.5–0.6, visualized by spraying the edge of the plate with aqueous cerric sulfate solution in 3N sulfuric acid followed by charring) is that of the epoxide diacetate. Removal of the bands from the plate followed by elution with ethyl acetate:cyclohexane (50:50) affords two products having the following spectral characteristics:

1. The $\alpha,\beta$-enone diacetate
I.R. (neat) $\mu$: 5.75, 5.95, 6.2, 8.1;
N.M.R. (CDCl$_3$-TMS) $\delta$: 1.0, 1.11, 2.03, 4.08, 4.56, 4.62, 5.2–5.5, 6.03.

2. The epoxide diacetate
I.R. (neat) $\mu$: 5.75, 5.85, 6.35, 7.25, 8.1, 8.6, 8.92, 9.7;
N.M.R. (CDCl$_3$-TMS) $\delta$: 1.0, 1.1, 1.2, 1.32, 2.0, 2.4–3.2, 4.07, 4.46, 4.60, 4.72, 5.33.

EXAMPLE 2

Deoxygenation with Zinc-Copper Couple

The epoxide diacetate obtained in Example 1 (45 mg.) is heated with zinc-copper couple (1.0 g.) in ethanol (30 ml.) at relux for 2 days. The metallic precipitate is filtered and the filtrate evaporated to dryness in vacuo to afford a diacetate compound having the following spectral characteristics:

I.R. (neat) $\mu$: 5.75 and 5.83
N.M.R. (CDCl$_3$-TMS) $\delta$: 1.0, 1.11, 1.6, 1.70, 2.03, 3.05, 3.17, 4.08, 4.50, 4.63, 5.1–5.5

EXAMPLE 3

Deoxygenation

A solution of the epoxide diacetate obtained in Example 1 (0.264 g.) in purified tetrahydrofuran (5 ml.) is treated with lithium diphenylphosphide (3.4 ml. of a 0.55 m. solution, for 20 hours at room temperature. Acetic acid (0.056 g.) is added to the mixture followed by the addition of methyl iodide (0.142 g.); the resultant mixture is allowed to stand for 0.5 hours at room temperature. Water is added and the organic phase is separated, dried and evaporated to afford a compound having the same spectral analysis as the diacetate compound obtained in Example 2.

EXAMPLE 4

Hydrolysis

A solution of the diacetate obtained in Example 2 (0.38 mg.) in methanol (10 ml.) is stirred at room temperature with a 10% potassium carbonate solution (0.6 ml.) under a nitrogen atmosphere for 19 hours. The solvent is removed in vacuo and the residue is extracted with methylene chloride and dried (Na$_2$SO$_4$). The solvent is evaporated under nitrogen to give an oily residue (24 mg.) which after purification by preparative thin layer chromatography (10:90 i - PrOH:CHCl$_3$) affords a utero-evacuant material having the following spectral characteristics:

I.R. (neat) $\mu$: 2.91, 5.88;
N.M.R. (CDCl$_3$-TMS) $\delta$: 1.04, 1.15, 1.67, 1.76, 2.18, 3.18, 3.58, 4.15, 4.26, 5.41.

EXAMPLE 5

Hydrolysis

Following the procedure of Example 4 but substituting an equivalent amount of the $\alpha,\beta$-enone diacetate obtained in Example 1 for the $\beta,\gamma$-enone diacetate obtained in Example 2, there is obtained a utero-evacuant material having the following spectral characteristics:

I.R. (neat) $\mu$: 5.75, 5.95, 6.2 and 8.1;
N.M.R. (CDCl$_3$-TMS) $\delta$: 1.0, 1.11, 2.03, 4.08, 4.56, 4.62, 5.2–5.5 and 6.03.

The following general procedure is employed to detect uterine contractions in female animals.

PROCEDURE I

Mature female New Zealand rabbits are anesthetized with sodium pentobarbital and ovariectomized. Following a recovery period of one week, the rabbits are treated with 5 $\mu$g./day s.c. of 17$\beta$-estradiol for 6 consecutive days, followed by treatment with 1.0 mg./day s.c. of progesterone for 7 consecutive days. The uterus and oviducts of the rabbits are perfused 72 hours after the last dose of progesterone according to the method of Heilman et al., (Fertil. Steril. 23:221–229) with slight modifications. The oviduct and uterus are perfused at a rate of 53 $\mu$l./min. The uterus is perfused with a tube extending 1.0 cm. into the lumen of the uterus from the oviducal end. The uterus is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

Intravenous administration of the compound obtained from Example 4 is effective in inducing uterine contractions and relaxing the oviduct in 72-hour progesterone withdrawn rabbits in a dose range of 1.0–4.0 mg./kg. The compound obtained from Example 5 is effective when administered in a dose range of from 25–40 mg./kg.

The following general procedure is employed to detect interruption of pregnancy after implantation has occurred.

PROCEDURE II

Mature, Hartley strain, female guinea pigs are continuously cohabited (monogamously) with males until a vaginal plug (copulation plug) is found in the cage. This time is considered to be day 1 of gestation. Groups of 5–6 females are given test materials intra-peritoneally in the vehicle described in Procedure 1 on day 22 of gestation. Pigs are sacrificed between the 25th and 45th day of gestation and examined for evidence of resorption or abortion.

Intra-peritoneal administration of the material obtained from Example 4 is effective in interrupting pregnancy when administered in a dose range from 25 –85 mg./kg.

What is claimed is:

1. The method of purifying extracts containing utero-evacuant materials obtained from the zoapatle plant which comprises the steps of:

reacting the semi-purified utero-evacuant materials with a peracid to epoxidize the $\beta,\gamma$-unsaturated system, chromatographing the reaction mixture over an adsorbent material, eluting the adsorbent material with a mixture of polar and non-polar organic solvents and collecting the fractions containing the epoxidized and unreacted utero-evacuant materials.

2. The method of claim 1 wherein the zoapatle plant is *Montanoa tomentosa* or *Montanoa floribunda*.

3. The method of claim 1 wherein the peracid is m-chloroperbenzoic acid.

4. The method of claim 1 wherein the adsorbent material is silica gel.

5. The method of claim 1 wherein the eluting solvent is a mixture of ethyl acetate and cyclohexane.

6. The method of claim 1 which additionally comprises reacting the epoxide with a deoxygenating agent to regenerate the $\beta,\gamma$-unsaturated keto system.

7. The method of claim 6 wherein the deoxygenating agent is zinc-copper couple.

8. The method of claim 6 wherein the deoxygenating agent is lithium diphenylphosphide.

9. The method of purifying extracts containing utero-evacuant materials obtained from the zoapatle plant which comprises the steps of:
reacting the semi-purified utero-evacuant materials with a reagent selected from an acylating agent and etherifying agents, reacting the ester or ether formed with a peracid to epoxidize the $\beta, \gamma$-unsaturated system, chromatographing the reaction mixture of polar and non-polar solvents and collecting the fractions containing the epoxidized and unepoxidized materials.

10. The method of claim 9 wherein the acylating agent is acetic anhydride.

11. The method of claim 9 wherein the acylating agent is acetyl chloride.

12. The method of claim 9 wherein the peracid is selected from m-chloroperbenzoic acid, peracetic acid and trifluoroperacetic acid.

13. The method of claim 9 which additionally comprises reacting the epoxide formed with a deoxygenating agent followed by removal of the protecting group by reaction with a hydrolyzing agent.

14. The method of claim 13 wherein the deoxygenating agent is zinc-copper couple, the hydrolyzing agent is potassium carbonate and the protecting group is an acyl moiety.

15. The method of claim 13 wherein the hydrolyzing agent is selected from acetic acid and trifluoroacetic acid and the protecting group is an ether.

16. The method of purifying extracts containing utero-evacuant materials obtained from the zoapatle plant which comprises selectively reacting the semi-purified utero-evacuant materials with a peracid to epoxidize the $\beta, \gamma$-unsaturated system and separating the epoxidized material from the reaction mixture.

* * * * *

UNITED STATES PATENT AND TRADEMARK OFFICE
CERTIFICATE OF CORRECTION

PATENT NO. : 4,060,604
DATED : November 29, 1977
INVENTOR(S) : Ramesh M. Kanojia It is certified that error appears in the above-identified patent and that said Letters Patent are hereby corrected as shown below:

In Column 2, line 48, "t-butyl" should read --- $\underline{t}$-butyl ---.

In Column 2, line 60, "t-butyl" should read --- $\underline{t}$-butyl ---.

In Column 3, line 45, "50°-75°c." should read --- 50°-75°C. ---.

In Column 3, line 61, title, "PREPARATION OF STATING MATERIAL" should read --- PREPARATION OF STARTING MATERIAL ---.

In Column 4, line 29, "in vacuo" should read --- $\underline{in\ vacuo}$ ---.

In Column 4, line 46, "in vacuo" should read --- $\underline{in\ vacuo}$ ---.

In Column 4, line 62, "in vacuo" should read --- $\underline{in\ vacuo}$ ---.

In Column 4, line 65, "m-chloroperbenzoic" should read --- $\underline{m}$-chloroperbenzoic ---.

In Column 5, line 29, "in vacuo" should read --- $\underline{in\ vacuo}$ ---.

In Column 5, line 59, "in vacuo" should read --- $\underline{in\ vacuo}$ ---.

In Column 5, line 63, " 10:90 i - PrOH:CHCl$_3$" should read 10:90 $\underline{i}$ - PrOH:CHCl$_3$ ---.

In Column 6, line 25, "(Fertil.Steril. 23: 221-229)" should read --- (Fertil.Steril. $\underline{23}$: 221-229) ---.

In Column 7, line 11, Claim 3, "m-chloroperbenzoic" should read --- $\underline{m}$-chloroperbenzoic ---.

UNITED STATES PATENT AND TRADEMARK OFFICE
CERTIFICATE OF CORRECTION

PATENT NO. : 4,060,604
DATED : November 29, 1977
INVENTOR(S) : Ramesh M. Kanojia It is certified that error appears in the above-identified patent and that said Letters Patent are hereby corrected as shown below:

In Column 8, line 2, Claim 9, after "mixture" and before "of" add --- over an adsorbent material, eluting the column with a mixture ---.

In Column 8, line 10, Claim 12, "m-chloroperbenzoic" should read --- m-chloroperbenzoic ---.

Signed and Sealed this

Fourth Day of July 1978

[SEAL]

Attest:

RUTH C. MASON
*Attesting Officer*

DONALD W. BANNER
*Commissioner of Patents and Trademarks*